(12) United States Patent
Hollister

(10) Patent No.: US 6,328,713 B1
(45) Date of Patent: *Dec. 11, 2001

(54) NEEDLE SHEATH DEVICE

(75) Inventor: William H. Hollister, East Sullivan, NH (US)

(73) Assignee: Sims Portex Inc., Keene, NH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/353,632

(22) Filed: Jul. 15, 1999

Related U.S. Application Data

(63) Continuation of application No. 08/047,182, filed on Apr. 16, 1993, now Pat. No. 5,993,426.

(51) Int. Cl.⁷ ...................................................... A61M 5/32
(52) U.S. Cl. .............................................................. 604/192
(58) Field of Search ..................................... 604/192, 263, 604/187, 198, 197, 164, 171, 162

(56) References Cited

U.S. PATENT DOCUMENTS

| Re. 31,086 | 11/1982 | Johnson, Jr. et al. . |
| 1,779,451 | 10/1930 | Sponsel . |
| 2,700,385 | 1/1955 | Ortiz . |
| 2,836,942 | 10/1958 | Miskel . |
| 2,854,976 | 10/1958 | Heydrich . |
| 2,953,243 | 9/1960 | Roehr . |
| 3,021,942 | 2/1962 | Hamilton . |
| 3,073,307 | 1/1963 | Stevens . |
| 3,074,542 | 1/1963 | Myerson et al. . |
| 3,255,873 | 6/1966 | Speelman . |
| 3,294,231 | 12/1966 | Vanderbeck . |
| 3,323,523 | 6/1967 | Scislowicz et al. . |

(List continued on next page.)

FOREIGN PATENT DOCUMENTS

| 1233302 | 5/1971 | (GB) . |
| 2239604 | 7/1991 | (GB) . |
| 2239607 | 7/1991 | (GB) . |
| 2240273 | 7/1991 | (GB) . |
| 2240477 | 7/1991 | (GB) . |
| WO 87/07162 | 12/1987 | (WO) . |
| WO 90/01348 | 2/1990 | (WO) . |
| WO 91/09637 | 7/1991 | (WO) . |
| WO 91/09638 | 7/1991 | (WO) . |
| WO 91/09639 | 7/1991 | (WO) . |

*Primary Examiner*—Manuel Mendez
(74) *Attorney, Agent, or Firm*—Louis Woo

(57) ABSTRACT

The safety device of the instant invention is equipped with a fluid absorbable material at the portion of the sheath that meets the tip portion of the needle so that, as the sheath is pivoted to a position in substantial alignment with the needle, whatever fluid that has been collected at the needle is absorbed before the needle is fixedly retained by a locking mechanism, either integrated within the needle sheath or to the base and lower portion of the needle sheath, to thereby prevent splattering or aerosolization of contaminated fluid into the environment.

22 Claims, 3 Drawing Sheets

U.S. PATENT DOCUMENTS

| | | |
|---|---|---|
| 3,329,146 | 7/1967 | Waldman, Jr. . |
| 3,333,682 | 8/1967 | Burke . |
| 3,342,319 | 9/1967 | Faulseit . |
| 3,367,488 | 2/1968 | Hamilton . |
| 3,485,239 | 12/1969 | Vanderbeck . |
| 3,537,452 | 11/1970 | Wilks . |
| 3,610,240 | 10/1971 | Harautuneian . |
| 3,658,061 | 4/1972 | Hall . |
| 3,828,775 | 8/1974 | Armel . |
| 3,890,971 | 6/1975 | Leeson et al. . |
| 3,904,033 | 9/1975 | Haerr . |
| 3,934,722 | 1/1976 | Goldberg . |
| 3,968,876 | 7/1976 | Brookfield . |
| 4,113,090 | 9/1978 | Carstens . |
| 4,139,009 | 2/1979 | Alvarez . |
| 4,175,008 | 11/1979 | White . |
| 4,300,678 | 11/1981 | Gyure et al. . |
| 4,375,849 | 3/1983 | Hanifl . |
| 4,430,082 | 2/1984 | Schwabacher . |
| 4,592,744 | 6/1986 | Jagger et al. . |
| 4,634,428 | 1/1987 | Cuu . |
| 4,643,722 | 2/1987 | Smith, Jr. . |
| 4,659,330 | 4/1987 | Nelson et al. . |
| 4,664,249 | 5/1987 | Landis . |
| 4,664,259 | 5/1987 | Landis . |
| 4,664,654 | 5/1987 | Strauss . |
| 4,681,567 | 7/1987 | Masters et al. . |
| 4,695,274 | 9/1987 | Fox . |
| 4,702,738 | 10/1987 | Spencer . |
| 4,723,943 | 2/1988 | Spencer . |
| 4,728,320 | 3/1988 | Chen . |
| 4,728,321 | 3/1988 | Chen . |
| 4,731,059 | 3/1988 | Wanderer et al. . |
| 4,735,311 | 4/1988 | Lowe et al. . |
| 4,735,618 | 4/1988 | Hagan . |
| 4,737,144 | 4/1988 | Choksi . |
| 4,738,663 | 4/1988 | Bogan . |
| 4,743,233 | 5/1988 | Schneider . |
| 4,746,008 | 5/1988 | Heverly et al. . |
| 4,747,836 | 5/1988 | Luther . |
| 4,747,837 | 5/1988 | Hauck . |
| 4,772,272 | 9/1988 | McFarland . |
| 4,778,453 | 10/1988 | Lopez . |
| 4,781,697 | 11/1988 | Slaughter . |
| 4,782,841 | 11/1988 | Lopez . |
| 4,790,828 | 12/1988 | Bombrowski et al. . |
| 4,793,484 | 12/1988 | Schoettle . |
| 4,795,432 | 1/1989 | Karczmer . |
| 4,795,443 | 1/1989 | Permenter et al. . |
| 4,801,295 | 1/1989 | Spencer . |
| 4,804,372 | 2/1989 | Laico et al. . |
| 4,813,426 | 3/1989 | Haber et al. . |
| 4,816,022 | 3/1989 | Poncy . |
| 4,816,024 | 3/1989 | Sitar et al. . |
| 4,819,659 | 4/1989 | Sitar . |
| 4,820,277 | 4/1989 | Norelli . |
| 4,826,490 | 5/1989 | Byrne et al. . |
| 4,826,491 | 5/1989 | Schramm . |
| 4,838,871 | 6/1989 | Luther . |
| 4,842,587 | 6/1989 | Poncy . |
| 4,846,796 | 7/1989 | Carrell et al. . |
| 4,850,968 | 7/1989 | Romano . |
| 4,850,976 | 7/1989 | Heinrich et al. . |
| 4,850,977 | 7/1989 | Bayless . |
| 4,850,978 | 7/1989 | Dudar et al. . |
| 4,850,994 | 7/1989 | Zerbst et al. . |
| 4,850,996 | 7/1989 | Cree . |
| 4,858,607 | 8/1989 | Jordan et al. . |
| 4,863,434 | 9/1989 | Bayless . |
| 4,863,435 | 9/1989 | Sturman et al. . |
| 4,863,436 | 9/1989 | Glick . |
| 4,867,746 | 9/1989 | Dufresne . |
| 4,872,552 | 10/1989 | Unger . |
| 4,874,383 | 10/1989 | McNaughton . |
| 4,874,384 | 10/1989 | Nunez . |
| 4,883,469 | 11/1989 | Glazier . |
| 4,886,503 | 12/1989 | Miller . |
| 4,888,001 | 12/1989 | Schoenberg . |
| 4,892,107 | 1/1990 | Haber . |
| 4,892,521 | 1/1990 | Laico et al. . |
| 4,900,309 | 2/1990 | Netherton et al. . |
| 4,927,019 | 5/1990 | Haber . |
| 4,944,397 | 7/1990 | Miller . |
| 4,976,699 | 12/1990 | Gold . |
| 4,982,842 | 1/1991 | Hollister . |
| 5,154,285 | 10/1992 | Hollister . |
| 5,188,611 | 2/1993 | Orgain . |

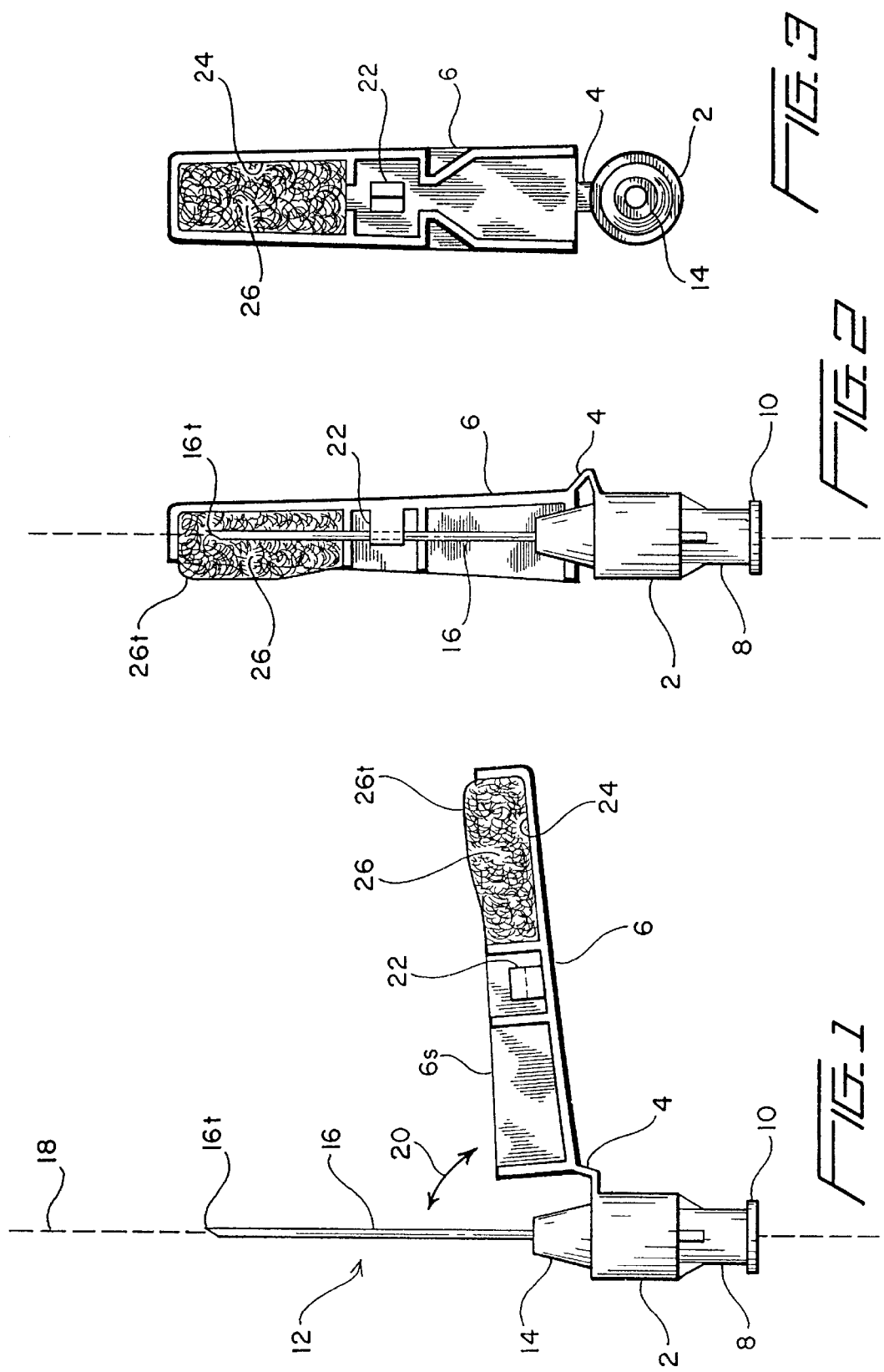

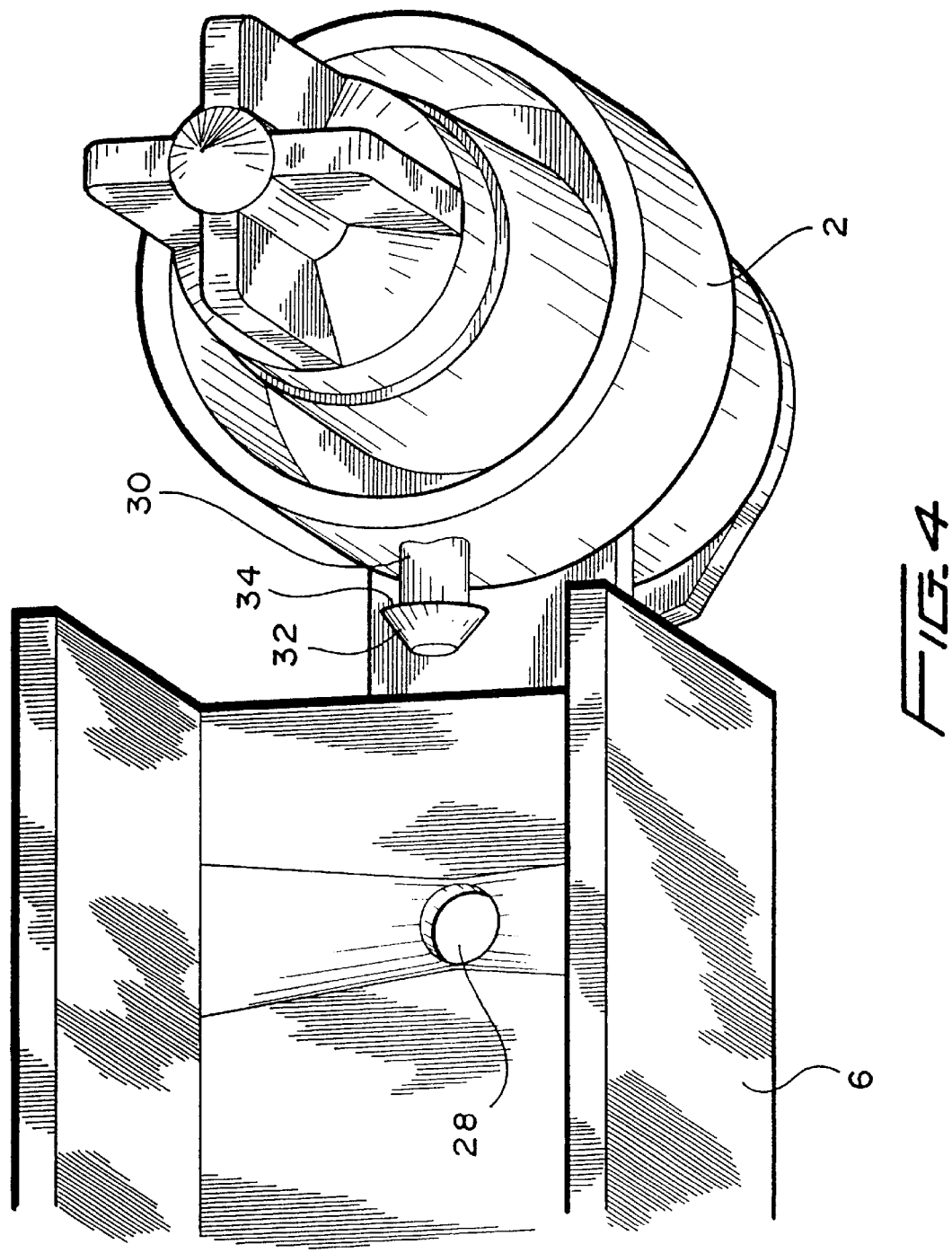

NEEDLE SHEATH DEVICE

This application is a Continuation of application Ser. No. 08/047,182 filed Apr. 16, 1993, now U.S. Pat. No. 5,993, 426.

This application is related to U.S. Pat. Nos. 5,615,771 and 5,649,622.

FIELD OF THE INVENTION

The instant invention relates to a safety device for housing a hypodermic needle to prevent the tip of the needle from being exposed after use and particularly to a needle sheath that includes a material for absorbing any fluid collected at the needle when the sheath is positioned to enclose the needle.

BACKGROUND OF THE INVENTION

In Hollister U.S. Pat. No. 4,982,842 there is disclosed a safety needle device comprising a housing hingedly connected to a base of the device. The housing is pivotable to a position in substantial alignment with a needle mated to the device so as to enclose the same. The '842 device has proven to be quite effective in preventing accidental needle pricks.

However, given the fact that fluid, such as for example blood or medicament, could potentially be collected at the needle, and more specifically at the tip thereof, it has been found that there is a high likelihood that the fluid at the needle could be splattered, splashed or aerosolized into the atmosphere when the protective housing is pivoted to enclose the needle. This is found to be particularly the case when the housing has integrated therein locking means, such as for example a hook, that snaps onto the needle for fixedly retaining the same as the housing is pivoted to be in substantial alignment with the needle. The fluid that gets aerosolized or atomized oftentimes is contaminated, as for example contaminated blood carrying the HIV virus. Accordingly, there is a need for a needle sheath that prevents fluid collected at the needle from splattering.

SUMMARY OF THE PRESENT INVENTION

The safety device of the present invention is an improvement of the '842 device. The disclosure of U.S. Pat. No. 4,982,842 is incorporated by reference herein.

Specifically, to overcome the potential aerosolization or splashing of fluid when a needle sheath is pivoted to enclose a contaminated needle, a fluid absorbable material yieldable to a needle pressed thereagainst is provided to the upper portion of the needle sheath so that, as the needle is being enclosed by the being pivoted needle sheath, the needle would contact the fluid absorbable material. To ensure contact, the absorbable material is configured such that a portion thereof extends to a position whereby, if the needle sheath were to have integrated thereto a locking mechanism that fixedly retains the needle when the needle sheath is pivoted to be in substantial alignment with the needle, the absorbable material would first contact the needle so that whatever fluid that may have been collected at the needle is absorbed thereby, before the needle contacts the locking mechanism. Insofar as fluid collected at the needle is absorbed by the fluid absorbable material before the needle contacts the locking mechanism, any vibration of the needle due to contact between the locking mechanism and the needle which otherwise would have flicked the fluid from the needle is prevented.

In a second embodiment of the instant invention, to ensure that the needle does not contact anything other than the fluid absorbable material, a combination latch mechanism is provided at the base and the lower portion of the sheath to prevent the sheath from moving relative to the base once the former has been pivoted to a position in substantial alignment with the latter. The latch combination may be in the form of an extension at the base that fittingly mates with an opening at the sheath for anchoring the sheath to the base once the sheath has been pivoted thereto. A variant of the latch locking mechanism comprises two opposed openings at the lower portion of the sheath which, when the sheath is pivoted to a position in substantial alignment with the base, lock onto two corresponding tabs formed at the base. Once locked to the base, the sheath is prevented from further relative movement with respect to the base.

It is therefore an objective of the present invention to provide a safety device that prevents aerosolization or splashing of blood when a needle sheath is pivoted to fixedly retain the needle.

BRIEF DESCRIPTION OF THE FIGURES

The above-mentioned objective and advantages of the present invention will become apparent and the invention understood by reference to the following description of the present invention taken in conjunction with the accompanying drawings, wherein:

FIG. 1 is a partially cut side view of the safety device of the present invention having its needle protection sheath pivoted away from the needle;

FIG. 2 is a partially cut-away view of the FIG. 1 device with the needle sheath having been pivoted to a position in alignment along the longitudinal axis of the needle/base;

FIG. 3 is a frontal view of the needle protection sheath of the instant invention;

FIG. 4 is a perspective view of the base and lower portion of the needle protection sheath of the instant invention in which a different locking mechanism is used.

DETAILED DESCRIPTION OF THE PRESENT INVENTION

Figure 5:
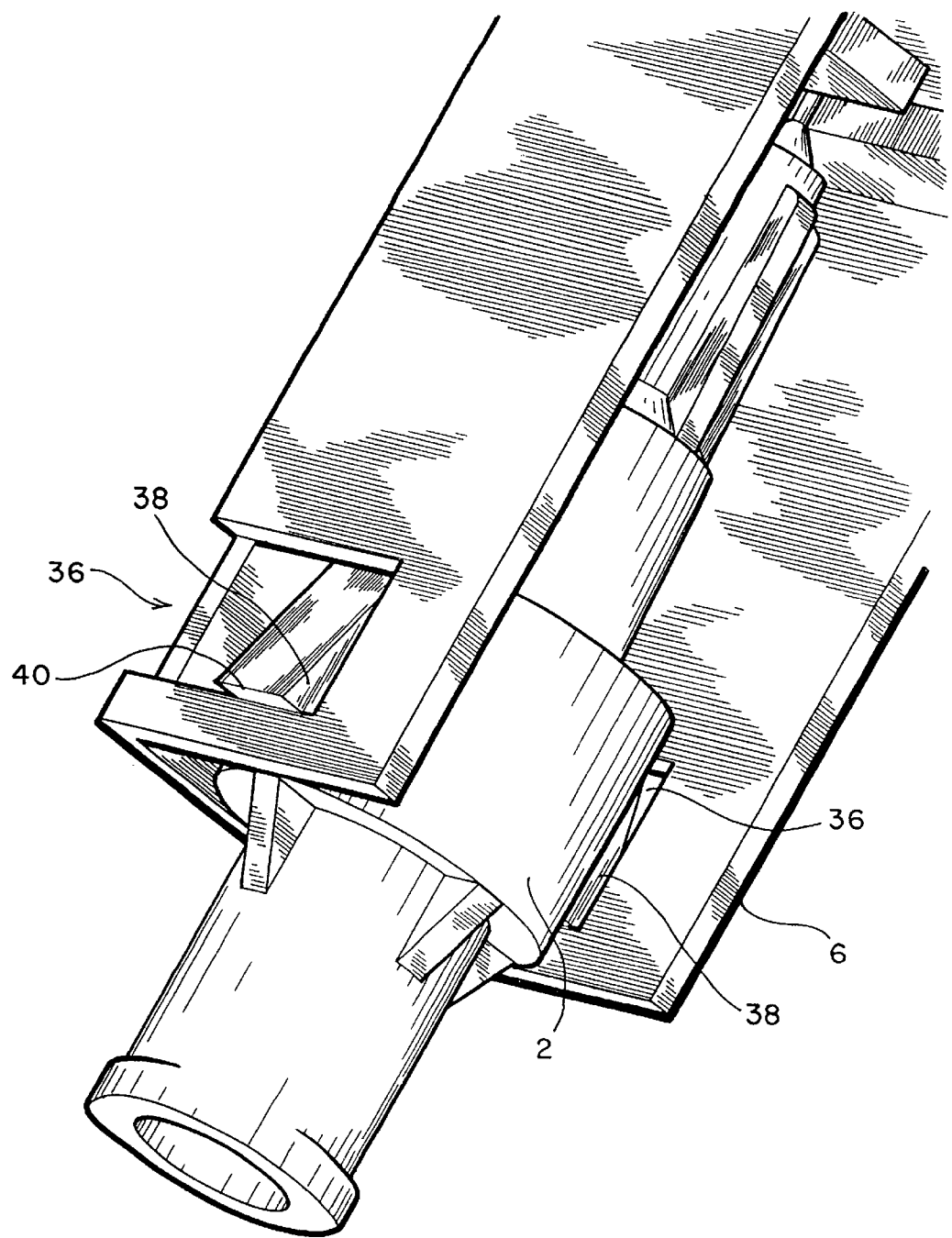
FIG. 5 is a perspective view of the base and lower portion of the needle sheath of the instant invention in which yet another type of locking mechanism is used.

A safety device of the instant invention is shown in FIG. 1. There, a base 2 is shown to have connected thereto, by means of a flexible strap or living hinge 4, a housing or sheath 6. Base 2 has an extension 8 to which a circumferential lip 10 is provided at its end for mating with a fluid container, for example a syringe (not shown). A needle assembly 12 is mated to the other end of base 2, by way of a hub 14. Thus, needle 16 is fixed to base 2 along a longitudinal axis, designated 18.

As shown by its partially cut view, sheath 6 is connected to base 2, by hinge 4, such that it is pivotable bi-directionally as indicated by bi-directional arrow 20. In FIG. 1, sheath 6 is shown to be at a position away from longitudinal axis 18 such that needle 16 may be used either to provide medicament to or withdraw blood from a patient. After use, oftentimes needle 16 has at tip 16t thereof (or at that portion of the needle) droplet(s) of blood.

Using FIG. 1 for illustration, before the instant invention, with a droplet of blood hanging from a needle, when a sheath (assume the needle and sheath of the aforementioned '842 device) is pivoted toward and snaps onto the needle, if too vigorous a snapping motion is used, the droplet of contaminated blood would be splashed or flicked into the atmosphere. Sometimes the blood droplet is aerosolized or atomized so that it forms a fine mist. Thus, an operator, or nearby bystanders, could be sprayed by the mist or droplet and potentially be exposed to contagious diseases possibly carried by the contaminated blood.

For the present invention, as shown, housing 6 has a locking mechanism, in the form of hook 22, integrated thereinto. For the sake of simplicity, only one hook 22 is shown. Of course, a plurality of hooks 22 may also be used. In any event, with reference to FIG. 3, sheath 6 is shown to have a large channel 24 into which a fluid absorbable material 26 is adapted. Material 26 is fixedly retained in the cavity provided by channel 24, as for example by bonding. Further, material 26 may be comprised of any of the many fluid absorbent materials such as foam, felt, cotton, paper, cloth, polyurethane foam, sponge, or other sufficiently soft fibrous materials yieldable to a relatively thin gauge flexible cannula, such as for example needle 16, biased thereagainst. In other words, when sheath 6 is pivoted toward axis 18, material 26 would be traversed by needle 16 until needle 16 is fixedly retained by hook 22 as disclosed in the '842 patent. Material 26 furthermore needs to be able to absorb at least its weight in fluid.

For the instant invention, material 26 is configured to contact needle tip 16t before the medial portion of needle 16 contacts hook 22. Thus, whatever fluid collected at needle tip 16t gets absorbed by material 26 before needle 16 is fixedly retained by hook 22, and fully enclosed by sheath 6. Thus, there is no fluid to be flicked from needle 16. As exaggeratedly shown in FIGS. 1 and 2, portion 26t of material 26 extends away from surface 6s of sheath 6.

In operation, when sheath 6 is pivoted toward axis 18 to envelop needle 16, any contaminated droplets of blood collected at tip 16t of needle 16 first contact material 26 at 26t and be absorbed thereby. Consequently, as sheath 6 is further moved toward axis 18 and be positioned in substantial alignment with needle 16 and base 2, even though needle 16 is snapped by hook 22, there is no splattering or flicking of any contaminated fluid from tip portion 16t. FIG. 2 shows the retention of needle 16 by hook 22 and the enclosure of the upper portion of needle 16 within material 26.

FIGS. 4 and 5 show respective different embodiments in which relative movement between sheath 6 and base 2 is prevented once sheath 6 has been pivoted to a position substantially in alignment with axis 18. For the FIGS. 4 and 5 embodiments, no hook 22 is provided within sheath 6. Accordingly, needle 16 does not contact anything other than material 26, even when sheath 6 is fully rotated to its alignment position per axis 18. The FIGS. 4 and 5 embodiments each prevent blood droplets from dripping from needle 16.

Specifically, in FIG. 4, an opening 28 is provided at the lower portion of sheath 6 while an anchor 30 extends from base 2. As shown, opening 28 and anchor 30 are situated such that when sheath 6 is pivoted toward base 2, anchor 30, and particularly its graduated tip 32, would pass through opening 28. Tip 32 of anchor 30 has a base 34 whose diameter is greater than that of opening 28. Consequently, once sheath 6 is positioned to its alignment position and opening 28 traverses past tip 32, base 34 would prevent sheath 6 from being pivoted in a direction away from base 2. Accordingly, sheath 6 remains at its alignment position enclosing needle 16, while the upper portion of needle 16 (not shown in FIGS. 4 and 5) is buried within material 26 and any fluid that may have been collected at needle tip 16t is absorbed by material 26.

In the FIG. 5 embodiment, instead of a single opening and a corresponding anchor, two openings 36 are provided at opposite sides of the lower portion of sheath 6 and two corresponding tabs 38 are integrated at base 2. As shown, each of tabs 38 has a slant configuration so that its base 40 prevents sheath 6 from moving away from base 2, once sheath 6 has been pivoted to be in substantial alignment with needle 16 for enveloping the same. Thus, openings 36 and tabs 38 cooperate to prevent further relative movement between sheath 6 and base 2 once tabs 40 are snap-locked to openings 36. Of course, material 26 adapted to sheath 6 of the FIGS. 4 and 5 embodiments could be configured as shown in FIGS. 1 and 2. Alternatively, inasmuch as there is no hook 22 integrated to sheath 6 and needle 16 does not come into contact with anything other than material 26, material 26 could be configured not to extend beyond surface 6s of sheath 6. Thus, any fluid that may drip from tip 16t of needle 16 is absorbed by material 26.

In as much as the present invention is subject to many variations, modifications and changes in detail, it is intended that all matter described throughout this specification and shown in the accompanying drawings be interpreted as illustrative only and not in a limiting sense. Accordingly, it is intended that the instant invention be limited only by the spirit and scope of the hereto appended claims.

What is claimed is:

1. A safety device, comprising:
    a base;
    a needle extending from said base;
    a housing pivotable from said base to a position for enveloping said needle; and
    coacting means at said base and said housing for latching with each other to prevent said housing from further movement relative to said base when said housing envelops said needle.

2. The safety device of claim 1, wherein said coacting means comprises:
    at least one aperture formed at said housing and at least one anchor means extending from said base for projecting through said aperture and anchoring said housing to said base when said housing is pivoted to envelop said needle.

3. The safety device of claim 1, wherein said coacting means comprises:
    openings formed at said housing fixedly mated to corresponding tabs formed at said base when said housing is pivoted to envelop said needle.

4. The safety device of claim 1, wherein said coacting means comprises:
    at least one pair of openings lockingly mating with corresponding pair of tabs when said housing is pivoted to envelop said needle.

5. The safety device of claim 1, wherein said coacting means comprises:
    a pair of openings formed at said housing;
    a pair of tabs provided at said base each coacting with a corresponding one of said openings for holding said housing relative to said base when said housing is pivoted to envelop said needle.

6. The safety device of claim 1, wherein said housing envelops said needle without contacting said needle.

7. The safety device of claim 1, further comprising:
    fluid absorber means provided in said housing for absorbing fluid on said needle as it makes contact with said needle when said needle is being enveloped by said housing.

8. A safety device, comprising:

a base having a first locking portion;

a housing having a second locking portion and pivotable to an alignment position to envelop a needle extending from said base;

wherein when said housing is pivoted to said alignment position, said first and second locking portions cooperate with each other to prevent said housing from further movement relative to said base.

9. The safety device of claim 8, wherein said first locking means comprises at least one anchor means extending from said base and said second locking means comprises at least one corresponding aperture formed at said housing such that, when said housing is pivoted to said alignment position, said anchor means projects through said aperture and is anchored thereto.

10. The safety device of claim 8, wherein said first locking portion comprises a pair of tabs and said second locking portion comprises a pair of corresponding openings for fixedly mating with said tabs when said housing is pivoted to said alignment position.

11. A needle protection apparatus, comprising:

a base;

a housing hingedly attached to said base, said housing being pivotable to a position substantially in alignment along the longitudinal axis of said base; and means at said base and said housing for latching with each other to prevent further relative movement between said housing and said base when said housing is pivoted to said alignment position.

12. Needle protection apparatus of claim 11, further comprising:

a needle extending from said base, said needle being enveloped by said housing when said housing is pivoted to said alignment position.

13. Needle protection apparatus of claim 11, wherein said latching means comprises:

at least one opening formed at said housing; and at least one corresponding tab formed at said base;

wherein said at least one opening and tab coact to fixedly maintain said housing relative to said base when said housing is pivoted to said alignment position.

14. Needle protection apparatus of claim 11, wherein said latching means comprises:

a pair of openings formed at said housing; and a corresponding pair of tabs formed at said base for fixedly mating with said openings when said housing is pivoted to said alignment position.

15. Needle protection apparatus of claim 11, wherein said coacting means comprises:

at least one aperture formed at said housing; and at least one anchor means extending from said base for projecting through said aperture to fixedly retain said housing to said base when said housing is pivoted to said alignment position.

16. Needle protection apparatus of claim 11, further comprising:

fluid absorber means provided in said housing for absorbing fluid on said needle as it makes contact with said needle when said needle is being enveloped by said housing.

17. A needle protection apparatus, comprising:

a base;

a housing hingedly attached to said base, said housing being pivotable to a position substantially in alignment along the longitudinal axis of said base;

a pair of locking means on opposite sides of said base, and a pair of locking means on opposite sides of said housing such that said locking means on said base and housing engage one another for preventing further relative movement between said housing and said base when said housing is pivoted to said alignment position.

18. Needle protection apparatus of claim 17, wherein said locking means on said base comprises a pair of tabs; and wherein said locking means on said housing comprises a pair of openings.

19. Safety apparatus, comprising:

a base;

a housing pivotable relative to said base; and a pair of locking means on opposite sides of said base, and a pair of locking means on opposite sides of said housing such that said locking means on said base and housing engage one another for preventing said housing from further moving away from said base when said housing is pivoted to said alignment position.

20. Needle protection apparatus of claim 19, wherein said locking means on said base comprises a pair of tabs; and wherein said locking means on said housing comprises a pair of openings.

21. A safety device, comprising:

a base wherefrom a needle extends;

a housing pivotable from said base to a position in alignment with said base for enveloping said needle; and a combination latching mechanism at said base and said housing for preventing said housing from further moving away from said base once said housing is pivoted to said alignment position.

22. Safety device of claim 21, wherein said latching mechanism comprises one pair of opposed latch portions at said housing and an other pair of latch portions at said base, said pairs of latching portions combining with each other to non-reversibly retain said housing to said base once said housing is pivoted to said alignment position.

* * * * *